(12) United States Patent
Pernot et al.

(10) Patent No.: US 9,474,585 B2
(45) Date of Patent: Oct. 25, 2016

(54) ENDODONTIC INSTRUMENT, THE ACTIVE PORTION OF WHICH HAS A SLOT FORMING A PASSAGE FOR A FLUID

(75) Inventors: Jacques Pernot, Vieilley (FR); Hubert Euvrard, Besancon (FR); Pierre Colon, Saint-Maur-des-Fosses (FR); Jean-Marie Vulcain, Vitre (FR)

(73) Assignee: NEOLIX, Chatres-la-Fort (FR)

( * ) Notice: Subject to any disclaimer, the term of this patent is extended or adjusted under 35 U.S.C. 154(b) by 207 days.

(21) Appl. No.: 13/825,170

(22) PCT Filed: Sep. 20, 2011

(86) PCT No.: PCT/EP2011/066338
§ 371 (c)(1),
(2), (4) Date: Jun. 12, 2013

(87) PCT Pub. No.: WO2012/038435
PCT Pub. Date: Mar. 29, 2012

(65) Prior Publication Data
US 2013/0260334 A1    Oct. 3, 2013

(30) Foreign Application Priority Data
Sep. 21, 2010  (FR) ...................................... 10 03743

(51) Int. Cl.
*A61C 5/04* (2006.01)
*A61C 5/02* (2006.01)

(52) U.S. Cl.
CPC *A61C 5/04* (2013.01); *A61C 5/023* (2013.01)

(58) Field of Classification Search
CPC ................................. A61C 5/04; A61C 5/023
USPC ..................................................... 433/81, 102
See application file for complete search history.

(56) References Cited

U.S. PATENT DOCUMENTS

| 993,100 | A | * | 5/1911 | Powers ............................ 279/89 |
| 3,330,040 | A | * | 7/1967 | Kahn ............................. 433/224 |
| 3,578,745 | A | * | 5/1971 | Garnier et al. ................ 433/102 |
| 3,906,636 | A | * | 9/1975 | Rainey et al. ................. 433/102 |
| 4,135,302 | A |   | 1/1979 | Kronman et al. |
| 4,636,171 | A | * | 1/1987 | Martin ........................... 433/134 |
| 4,832,061 | A | * | 5/1989 | Hwang .......................... 132/329 |
| 4,850,867 | A | * | 7/1989 | Senia et al. ................... 433/102 |

(Continued)

FOREIGN PATENT DOCUMENTS

| DE | 102006007316 A1 | 8/2007 |
| EP |     1110513 A2 | 6/2001 |
| WO |   2005122943 A2 | 12/2005 |

OTHER PUBLICATIONS

Supplemental French Search Report dated Sep. 19, 2013 for corresponding French Application No. 1003743, filed Sep. 21, 2010.

(Continued)

*Primary Examiner* — Cris L Rodriguez
*Assistant Examiner* — Hao D Mai
(74) *Attorney, Agent, or Firm* — David D. Brush; Westman, Champlin & Koehler, P.A.

(57) ABSTRACT

The invention relates to an endodontic instrument used for working on a canal in a tooth, having a base from which an active portion for working on the canal extends longitudinally, characterized in that said active portion has at least one slot extending longitudinally and forming a passage for fluid.

19 Claims, 8 Drawing Sheets

(56) References Cited

U.S. PATENT DOCUMENTS

| | | | | |
|---|---|---|---|---|
| 5,690,634 | A * | 11/1997 | Muller | A61B 17/164 606/180 |
| 5,879,160 | A * | 3/1999 | Ruddle | A61C 5/026 433/102 |
| 5,899,693 | A * | 5/1999 | Himeno et al. | 433/119 |
| 6,085,761 | A * | 7/2000 | Inaba | 132/329 |
| 6,162,202 | A * | 12/2000 | Sicurelli et al. | 604/272 |
| 6,162,226 | A * | 12/2000 | DeCarlo, Jr. | A61B 17/164 408/202 |
| 6,343,929 | B1 * | 2/2002 | Fischer | 433/81 |
| 6,443,730 | B2 * | 9/2002 | Davidson | 433/102 |
| 6,575,748 | B1 * | 6/2003 | Filhol | 433/102 |
| 6,579,092 | B1 * | 6/2003 | Senia et al. | 433/102 |
| 6,589,052 | B1 * | 7/2003 | Wilcko | 433/102 |
| 6,902,399 | B2 * | 6/2005 | Mannschedel | 433/141 |
| 7,040,893 | B2 * | 5/2006 | Fischer | 433/80 |
| 7,713,059 | B2 * | 5/2010 | Hof et al. | 433/102 |
| 7,833,017 | B2 * | 11/2010 | Hof et al. | 433/224 |
| 8,109,763 | B2 * | 2/2012 | Levy et al. | 433/102 |
| 8,235,719 | B2 * | 8/2012 | Ruddle et al. | 433/81 |
| 8,647,116 | B2 * | 2/2014 | Becker et al. | 433/102 |
| 2003/0130626 | A1 * | 7/2003 | VanTassel et al. | 604/272 |
| 2003/0207231 | A1 * | 11/2003 | Nance | 433/81 |
| 2005/0135888 | A1 * | 6/2005 | Stokey | B23B 51/0009 408/230 |
| 2006/0127843 | A1 | 6/2006 | Rosenblood et al. | |
| 2007/0054238 | A1 * | 3/2007 | Hof et al. | 433/102 |
| 2010/0105004 | A1 * | 4/2010 | Levy et al. | 433/102 |
| 2011/0190803 | A1 * | 8/2011 | To | A61B 17/1671 606/180 |
| 2012/0219927 | A1 * | 8/2012 | Maxwell | A61C 5/023 433/102 |
| 2012/0231413 | A1 * | 9/2012 | McSpadden et al. | 433/102 |

OTHER PUBLICATIONS

International Search Report and English translation from the International Searching Authority dated Dec. 20, 2011 for corresponding International Patent Application No. PCT/EP2011/066338, filed Sep. 20, 2011.

French Search Report and Written Opinion dated May 3, 2011 for corresponding French Patent Application No. 1003743, filed Sep. 21, 2010.

International Preliminary Report on Patentability and English Translation of the Written Opinion from the International Searching Authority dated Mar. 26, 2013 for corresponding International Application No. PCT/EP2011/066338, filed Sep. 20, 2011.

* cited by examiner

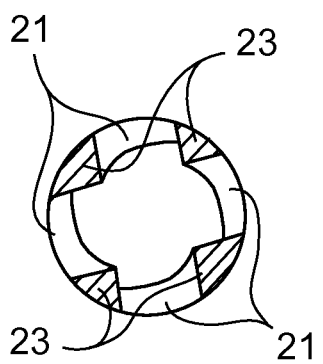 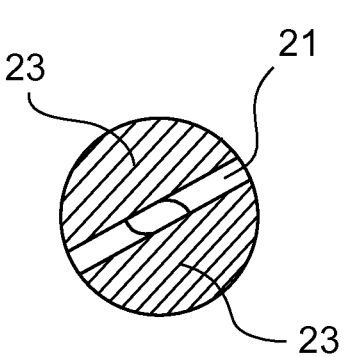 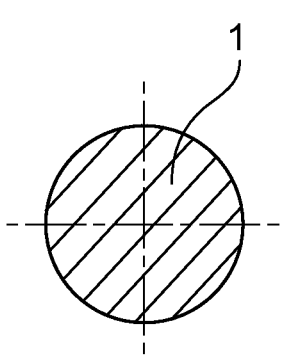
Fig. 22    Fig. 23    Fig. 24
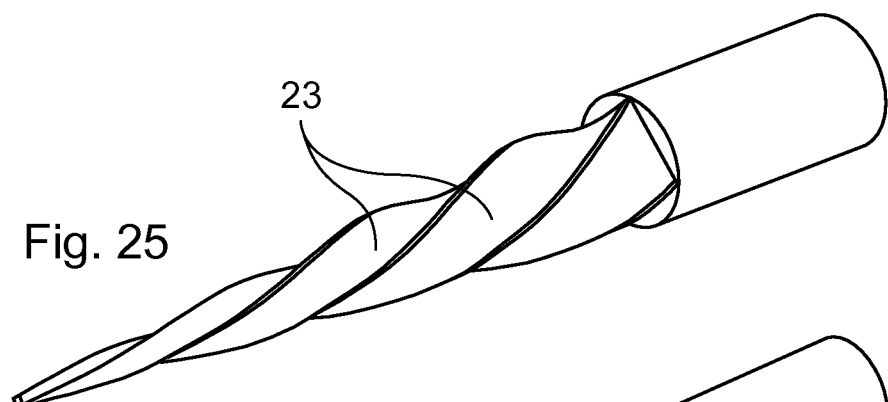
Fig. 25
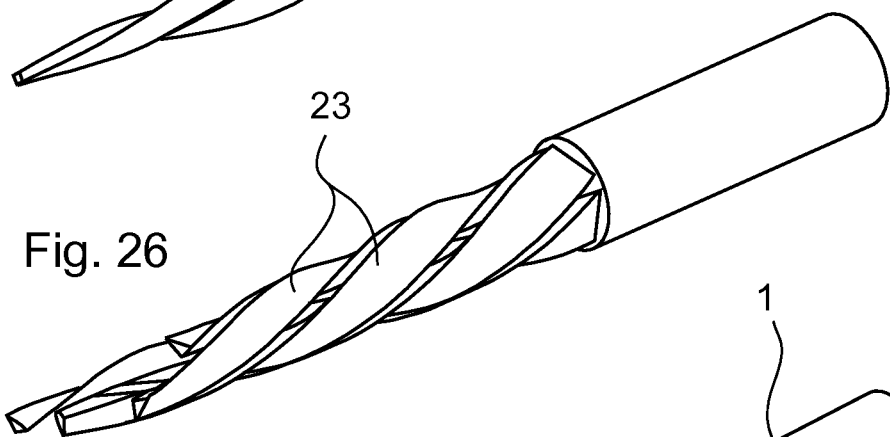
Fig. 26
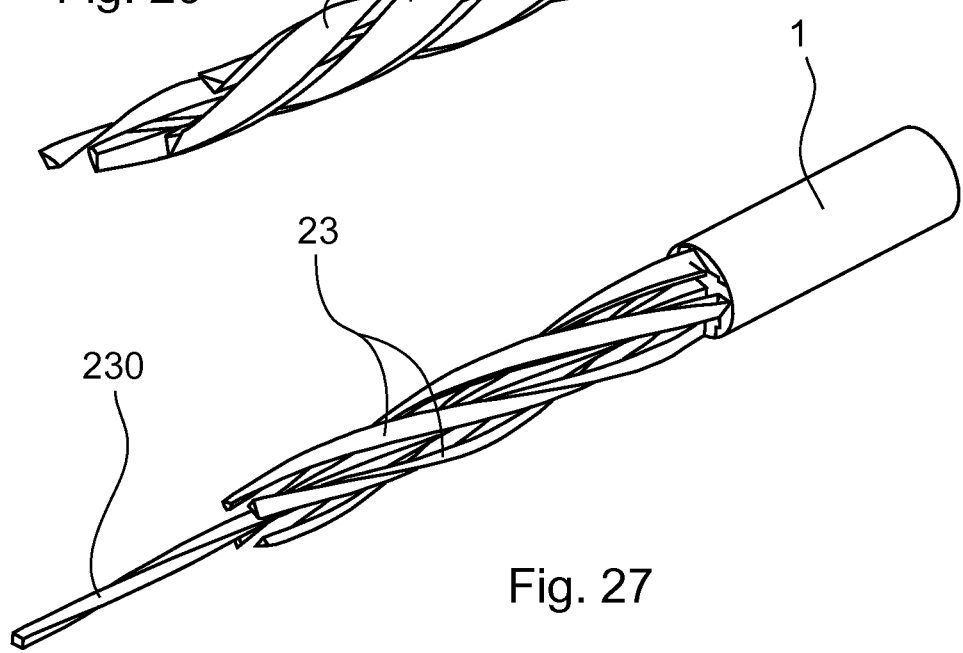
Fig. 27

ENDODONTIC INSTRUMENT, THE ACTIVE PORTION OF WHICH HAS A SLOT FORMING A PASSAGE FOR A FLUID

CROSS-REFERENCE TO RELATED APPLICATION

This Application is a Section 371 National Stage Application of International Application No. PCT/EP2011/066338, filed 20 Sep. 2011 and published as WO/2012/038435 on 29 Mar. 2012, in French, the contents of which are hereby incorporated by reference in their entirety.

FIELD OF THE DISCLOSURE

The field of the disclosure is that of the designing and manufacture of instruments for dental therapy. More specifically, the disclosure pertains to endodontic instruments used to work on canal in a root of a tooth (or dental root canal).

BACKGROUND OF THE DISCLOSURE

When a tooth is affected by deep decay, it is sometimes necessary to devitalize the tooth. To this end, it is necessary to remove infected tissues from the tooth and from the root of the tooth and shape a canal that is to be filled by a material constituted by gutta-percha or other canal filler pastes.

Endodontic instruments are used to perform these operations. These instruments can be likened to small-diameter drills which are used to ream and/or cut out the dentine from the root of the tooth to shape the canal that has to receive the gutta-percha or other canal filling pastes.

This treatment is therefore done in a mechanized way and the endodontic instruments are planned, at the time of their design, to have a hardness sufficient to go through the dentine which is a semi-hard material, while at the same time having a certain degree of flexibility to be able to take the internal shape of the root of the tooth. To this end, the endodontic instruments proposed for several years now have been made out of a nickel-titanium alloy instead of steel wire.

Present-day endodontic instruments are generally manufactured from a cylindrical rod on which one or more helical cuts are made, conventionally by means of a milling method. The cutting surfaces generate a cutting edge at their intersection.

With the classic means of grinding or milling, the cutting operations performed result from the combining of simultaneous motions of rotation and a forward movement of the wire (the part to be machined) before the grinder or the cutter. The instruments thus machined have a known geometry (circle, square, polygon, etc) in their section perpendicular to the axis of the wire, predetermined by the machining cycle. The centers of all these cross-sections together define the load-bearing core of the cutting edge along the cutting portion of the instrument. The result of the use of classic machining means (grinding or milling) is that this load-bearing core extends rectilinearly and coincidentally with the axis of the wire constituting the initial part to be machined.

The instruments used at present require great vigilance and precise dexterity on the part of the practitioner. Indeed, two mutually contrary phenomena can arise with known endodontic instruments:

either the edge of the endodontic instrument slips on the material of the dentine;

or the edge of the endodontic instrument gets engaged far too rapidly in the material of the dentine, leading to the phenomenon of overtight screwing, at the end of which the instrument gets jammed in the material.

In both cases, the machining of the canal is not done accurately or even is not done at all.

It must be noted that when the endodontic instrument gets jammed in the material, it frequently happens that the instrument breaks. Now the breaking of the endodontic instrument inside the canal results in major excess cost of operation for the practitioner and a risk to the patient's health.

Besides, it is classic to use fluid during the reaming of a canal, and this fluid should possibly be a lubricant liquid or an antiseptic solution.

However, presently used-day instruments considerably limit the effect of these fluids. Indeed, when reaming a tooth canal, the diameter of the canal is that of the instrument used and therefore the space between the wall of the canal and the rotating instrument does not enable the flow of a fluid. In certain cases, the shape of the flutes of the active part of the instrument even tends to drive the fluid out of the canal.

In any case, the effect of the fluid proves to be very limited in practice.

It is therefore necessary for the practitioner to carry out the reaming and irrigating operations separately, in interposed them, and this slows down the work.

The discussion above is merely provided for general background information and is not intended to be used as an aid in determining the scope of the claimed subject matter.

SUMMARY

This summary and the abstract are provided to introduce a selection of concepts in a simplified form that are further described below in the Detailed Description. The summary and the abstract are not intended to identify key features or essential features of the claimed subject matter, nor are they intended to be used as an aid in determining the scope of the claimed subject matter.

It is an aim of the disclosure especially to overcome the drawbacks of the prior art.

More specifically, the disclosure is aimed at proposing an endodontic instrument that especially increases the flow of a fluid in the tooth canal in which the instrument moves in order to be able to carry out the drilling and canal flushing operations simultaneously.

It is also an aim of the disclosure to provide an endodontic instrument of this type that is more efficient than those of the prior art and is simpler to use for the practitioner.

These goals as well as others that shall appear here below are achieved by means of the disclosure, an object of which is an endodontic instrument used to work a canal in a tooth, having a base from which there longitudinally extends an active part for the working of the canal, characterized in that the base and/or said active part at least partially has at least one slot extending longitudinally and forming a passage for fluid.

According to one advantageous application, the disclosure pertains to an endodontic instrument used to make a canal in a tooth, having a base from which there extends at least one flute between two cutting edges, said flute extending longitudinally along a cutting portion, the base and/or said cutting portion having at least partially at least one slot extending longitudinally and forming a passage for fluid.

Such a passage enables the flow of a fluid on all or part of the height of the endodontic instrument, whether in the canal entry direction (influx) or the canal exit direction (efflux).

An endodontic instrument according to the disclosure can therefore enable the irrigating of the root canal more efficiently than the prior-art instruments.

However, it can be noted that the disclosure is not intended exclusively for making a canal. Indeed, it can be imagined that an instrument using the principle of the disclosure would be designed and used for filling a canal with a filler paste (gutta-percha). Indeed, such a paste can be loaded into the instrument which will exert a thrust on the paste into the root canal, the surplus paste rising up by the exterior of the instrument.

Besides, in certain embodiments, some of which are described in greater detail here below, the making of the slot or slots can be such that it leads to the obtaining of an endodontic instrument capable of volumetric variations in its active part.

The active part can be made out of a single piece.

According to a first approach of the disclosure, the slot is at least partially helical.

Thus, the fluid irrigation flow is arranged jointly by the direction of the internal helix (that of the slot) or of the external helix (that of the flutes) and by the sense of rotation of the instrument.

Furthermore, an at least partially helical slot enables the fluid to be conveyed actively, whether in the same incoming or outgoing sense, as a function of the orientation of the helix (leftward or rightward).

Furthermore, the pitch of the helix influences the internal pressure and restores a dynamic flow to the fluid. The diameters of the at least partially helical slots partly characterize the flow-rate of the fluid.

According to another approach of the disclosure, said slot has a shape belonging to the following group:
sinusoidal;
rectilinear;
oblique;
curved;
non-straight, especially shaped as an L, S, T, U, V, W, Y, Z.

According to one particular embodiment, said slot has a radial opening.

According to another particular embodiment, said slot has an axial opening.

It can be noted that the (radial or axial) opening can be situated at any height on the instrument. This opening can be oriented towards the tip or towards the base of the instrument or towards neither (this is the case for example when a slot portion is perpendicular to the axis of the instrument).

Furthermore, it must be noted that the opening of the slot is not necessarily situated at the end of the slot. The opening can therefore be situated at any unspecified height between the two ends of the slot (for example in the case of a T-shaped or Y-shaped slot).

Naturally, the opening of the slot can also be situated at the end of the slot (on the tip or on the base).

It can also be envisaged that the slots will have no opening in the longitudinal sense.

According to one particular embodiment, in which the base has an axis of rotation, said slot extends longitudinally so as to be centered on said axis of rotation. However, according to another embodiment that can be envisaged, said slot extends longitudinally so as to be off-centered relative to said axis of rotation of the base.

According to one advantageous characteristic, said base also has at least one slot communicating with the slot of the active part.

In this way, the slot or slots made on the sleeve can make it possible to connect the irrigating system of the endodontic instrument to be connected with an external device, for example to convey a fluid from an external container towards the interior of the instrument and therefore, thereafter, towards the dental root canal being treated.

According to a preferred embodiment, said active part has at least one plurality of slots extending longitudinally, said active part having a plurality of demarcating arms between said plurality of slots.

In this case, said arms are preferably each borne by a load-bearing core extending along a path that is at least partially helical.

Such an instrument, with its plurality of arms borne by a helical load-bearing core, is liable to undergo volumetrical variations.

Indeed, the arms are liable to approach each other or to move away from each other radially. Furthermore, each end of the arms can be prepared so as to give a frontal cutting capacity (end cutting) as explained in greater detail here below.

This capacity for volumetrical variation results in an instrument according to this embodiment that gives especially the following advantages:

it prevents the jamming phenomenon and enables the natural disengagement of the tool by radial retraction in the event of great stress on the arms;

the relative variation of the instrument improves the removal of tooth debris and increases the efficiency of the irrigating fluid;

the effect of the instrument can be likened rather to a "scraping" or a grinding when compared with the action of classic endodontic instruments which can be likened to a simple cutting;

the tool can be adapted to the morphology of the canal which is variable and often complex (ovoid, dissymmetrical, irregular, with narrowing or widening, curvature, etc); thus the contact zone is always the maximum between the cutting edge or edges of the instrument and the wall of the canal through a natural permanent adjustment of the envelope curve plotted by the instrument in rotation under the effect of the stresses which are exerted on the instrument;

the tool performs a more selective curettage of the necrotic tissues, which are softer, because the force that these tissues present against the instrument is smaller than that of the healthy tissues which are firmer, thus preserving the shape of the treated canal in an optimized way;

the presence of several helices (those of the arms and those of the slot or slots), in identical or opposite directions, in the sense of rotation of the instrument or in the opposite sense, enables action on the incoming or outgoing circulation of the fluids (reaming, removal of debris, irrigation, compacting, etc).

According to an advantageous solution, said arms demarcate an axial hollow feature.

In this case, said axial hollow feature demarcated by said arms preferably communicates with an axial hollow feature made in said base.

According to one particular characteristic, said arms have different lengths.

In this case, one of said arms is advantageously a central arm with a length greater than that of the other arms.

Such a central arm can have the function of a "guide" or in other words a function of a "driver" of the instrument.

According to another particular characteristic, each of said arms has a notched end, for example to give them a frontal cutting power.

Such ends form a sort of grip capable of being used for example, by means of the instrument, to grip an undesirable element (such as a fragment of an instrument broken in a dental root canal).

DESCRIPTION OF THE DRAWINGS

Other characteristics and features of the disclosure shall appear more clearly from the following description of different embodiments of the disclosure, given by way of simple, illustratory and non-exhaustive examples and from the appended drawings, of which:

FIGS. 21 to 24 are views of an endodontic instrument according to a sixth embodiment of the disclosure, seen respectively in a side view and in three cross-sections;

FIG. 25 is a view of the instrument illustrated by FIG. 21, under radial stress;

FIG. 26 is a view in perspective of a variant of an embodiment of the endodontic instrument illustrated by FIG. 21;

FIGS. 27 to 32 are views of another alternative embodiment of the endodontic instrument illustrated by FIG. 21;

DETAILED DESCRIPTION

As indicated here above, the principle of the disclosure lies in the fact of proposing an endodontic instrument, the active part of which has a longitudinal slot dedicated to enabling the flow of a fluid.

According to one particular embodiment of the disclosure, the endodontic instrument is capable of undergoing volumetrical variations.

FIGS. 1 to 8 show two examples of embodiments of an endodontic instrument for working on a dental root canal, the instrument having a longitudinal slot according to the principle of the disclosure.

The term "working on a dental root canal" is understood to refer to several possible distinct situations, namely in particular actions consisting in drilling a canal or again filling a canal, i.e. the action of filling a canal with a filling paste.

As illustrated in FIGS. 1 to 8, an endodontic instrument has a base 1 which can constitute either a grasping end designed to be manipulated by hand by a practitioner, or an assembling unit to mount the endodontic instrument on a tip of a rotating tool.

The endodontic instrument according to the disclosure is made from a metal rod and more specifically from a rod made out of a nickel-titanium alloy, machined by an electrical discharge machine (EDM) technique. The EDM wire is shifted in a combination of longitudinal and transversal shifts relative to the longitudinal axis of the endodontic instrument, so as to generate cutting surfaces which, at their intersection, lead to the appearance of a cutting edge that extends longitudinally along a cutting portion 2 extending between two ends, one of which is defined by the base 1 of the instrument and the other by the distal end 1, opposite the base.

FIGS. 1 to 8 are views of two examples of metal rods constituting blanks of endodontic instruments.

According to the example illustrated by FIGS. 1 to 4, the blank piece is a hollow rod with a circular section. This blank piece furthermore has two slots 21 extending longitudinally, in this case helically, in the cutting portion (constituting the active part of the instrument). Such a blank piece is the part on which the flutes and cutting edges (a flute being demarcated by two cutting edges) are made.

Figure 1:
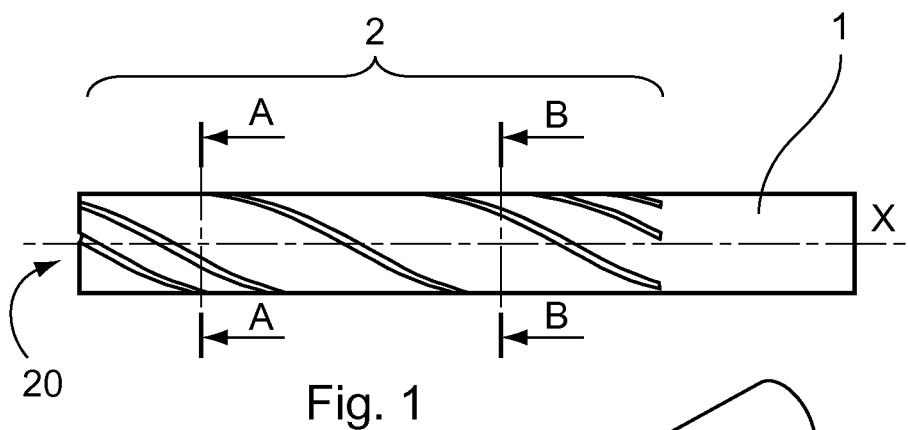
FIGS. 1 to 4 are views of a blank of an endodontic instrument according to a first embodiment of the disclosure, seen respectively from the side, in perspective and in two cross-sections.
Figure 2:
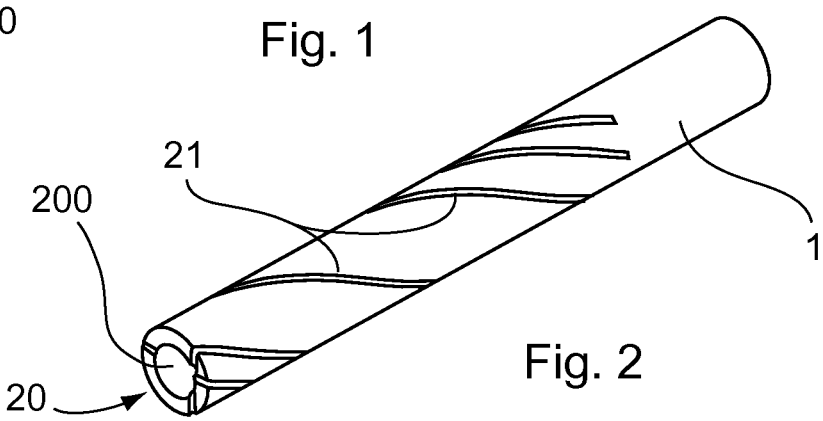
Figure 3:
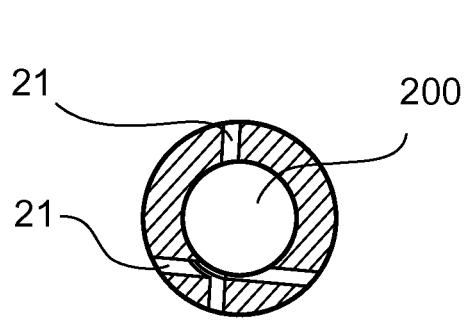
Figure 4:
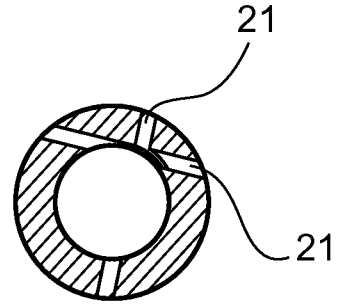

As can be seen in FIG. 3 (which is a view along the section AA indicated in FIG. 1) and in FIG. 4 (which is a view along the section BB indicated in FIG. 1), the slots 21 extend so as to be off-centered relative to the longitudinal axis X of the instrument, constituting the rotation axis of the base 1 of the instrument.

The slots thus made are passages for the circulation of a fluid such as an irrigation fluid. It can be noted that, according to the present embodiment, the instrument has a central hollow feature 200 also contributing the circulation of the fluid.

Figure 5:
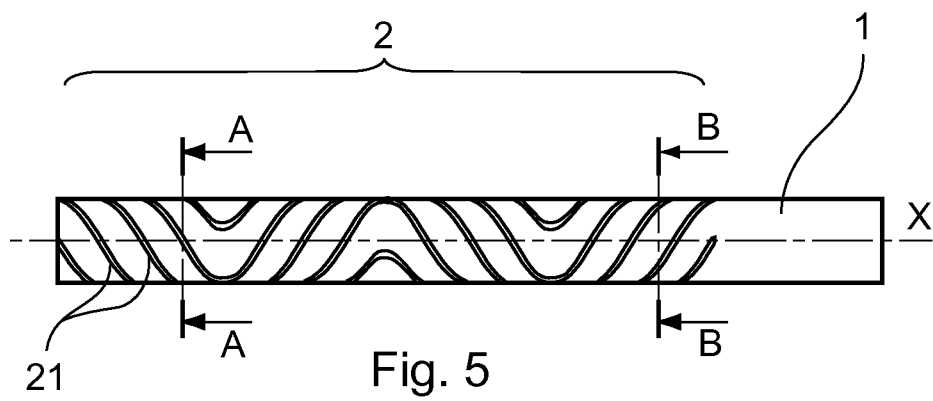
FIGS. 5 to 8 are views of a blank of an endodontic instrument according to a first embodiment of the disclosure, seen respectively from the side, in perspective and in two cross-sections.
Figure 6:
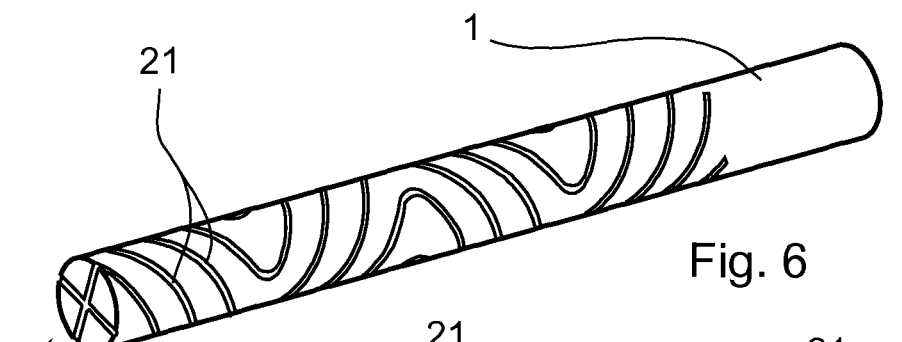
Figures 7, 8:
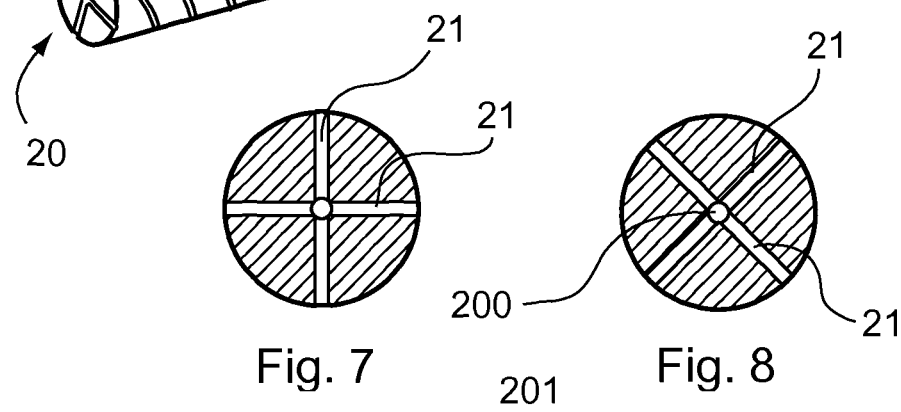

According to the embodiment illustrated in FIGS. 5 to 8, the blank part is made out of a solid rod and, in the cutting portion 2, it has two slots 21 extending longitudinally. As can be seen in FIGS. 5 and 6, the slots 21 have a sinusoidal shape. Referring to FIG. 7 (which is a view along the section AA indicated in FIG. 5), the slots extend longitudinally so as to be centered on the axis X of rotation of the base 1 of the instrument, thus characterizing a central hollow feature 200 (FIG. 8).

Figure 36:
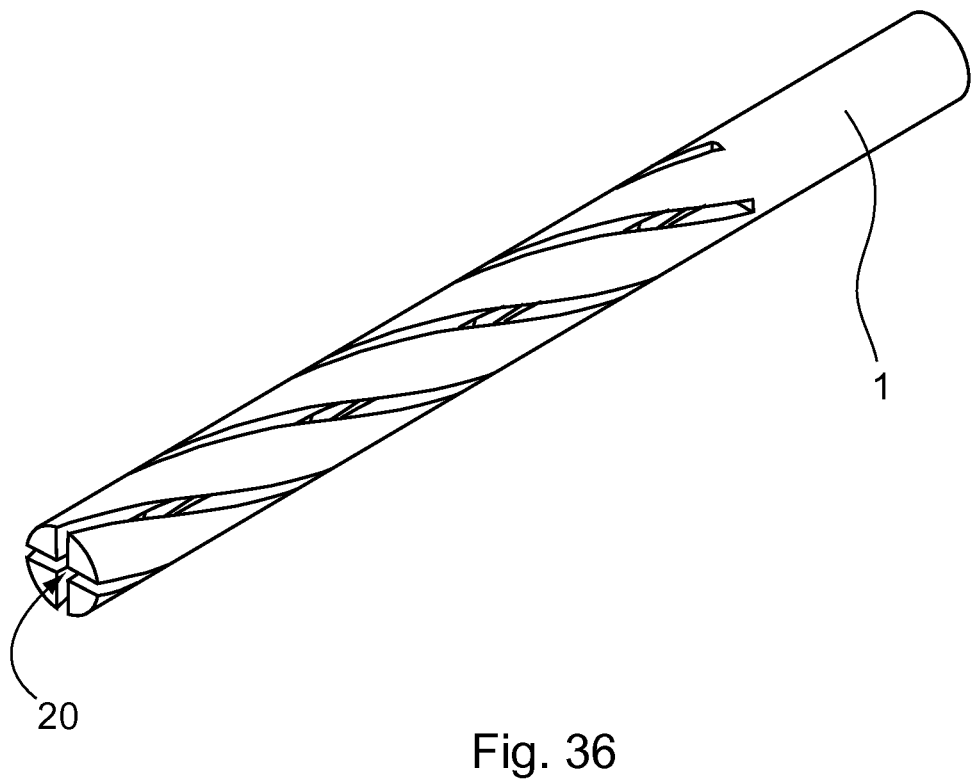
FIG. 36 is a view of another alternative embodiment of the instrument according to the disclosure.

It must be noted that the position of this hollow feature 200 can vary as a function of the centering or off-centering of the electrical discharge machining wire relative to the axis of rotation of the base 1 (FIG. 36).

Depending on the number of slots and their location relative to the centre or to the axis of rotation, at least two configurations are possible:

with central hollow feature (FIG. 36):

The slots are centered or off-centered by at least a radius of the electrical discharge machining wire;

with "driver" arm (FIG. 27):

The hollow feature in this case can be ring-shaped, with at least one slot off-centered by more than the radius of the electrical discharge machining wire.

In this configuration, a minimum of three slots have to be used. FIG. 27 illustrates four slots off-centered by more than the radius of the electrical discharge machining wire, revealing a guide arm or "driver" arm 230 centered on the axis of rotation of the base and having a length greater than that of the other external arms 23 (i.e. distributed around the "driver" arm 230).

This "driver" arm with a polygonal section can be formed by rectilinear and/or curved lines.

Figure 28:
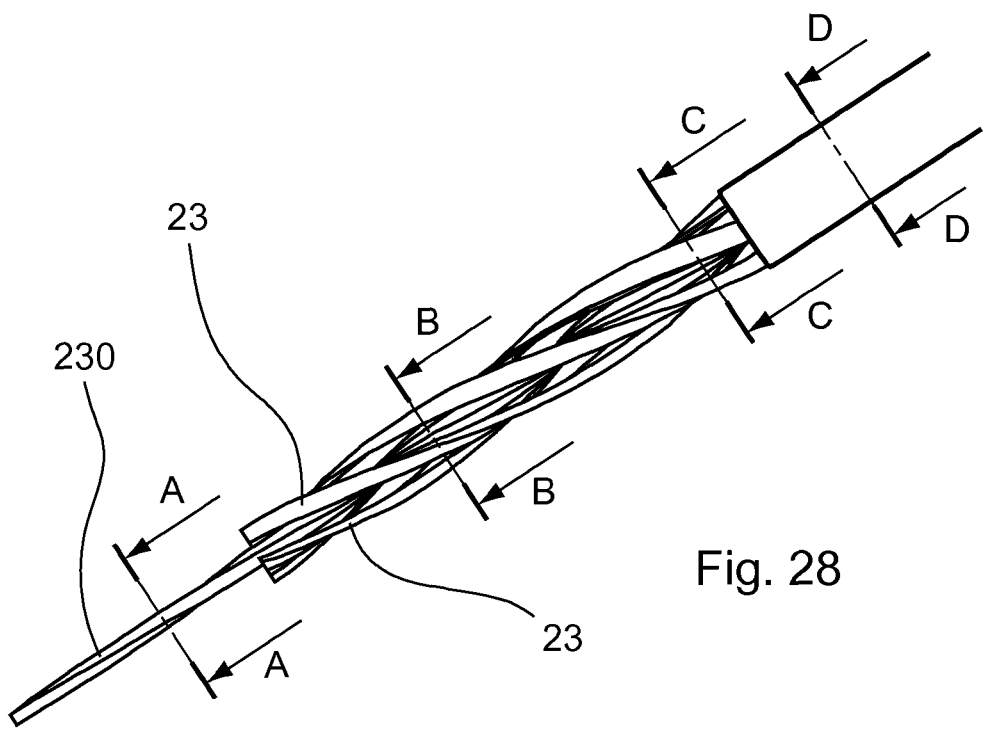
Figures 31, 32:
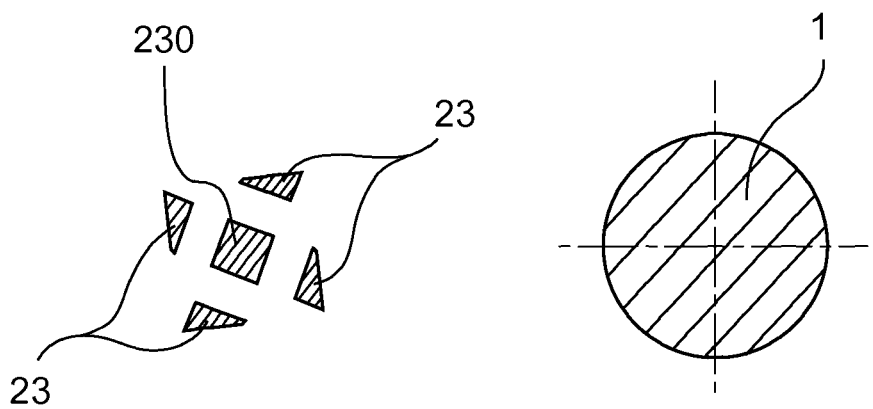

A more detailed description is given here below of the embodiment illustrated by FIG. 27 with the help of FIGS. 28 to 32 which show the instrument:
- in a side view (FIG. 28);
- along the section A-A indicated in FIG. 28 (FIG. 29);
- along the section B-B indicated in FIG. 28 (FIG. 30);
- along the section C-C indicated in FIG. 28 (FIG. 31);
- along the section D-D indicated in FIG. 28 (FIG. 32).

Figures 29, 30:
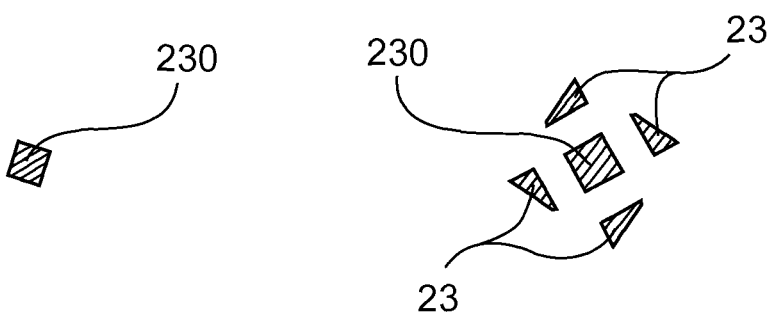

As can be seen in these figures, the sections of the "driver" arm 230 and the external arms 23 can be of any unspecified shape and/or upgradeable (FIGS. 29 to 31).

According to the present embodiment for example, the "driver" arm 230 has a square section while the arm 23 has a section in the form of a right-angled trapezium.

Besides, the end of the "driver" arm and the external arms can be provided with a cutting or non-cutting tip.

Other configurations can be envisaged with one or two slots which may be centered or not centered.

This specimen can be totally partially or not at all helical.

In a preferred embodiment, the distal end of the specimen is non-helical, conical and rounded at the tip and on the edges to clear a non-working part on a height of 3 mm for example, thus serving as the "driver" for the endodontic instrument.

Figure 35:
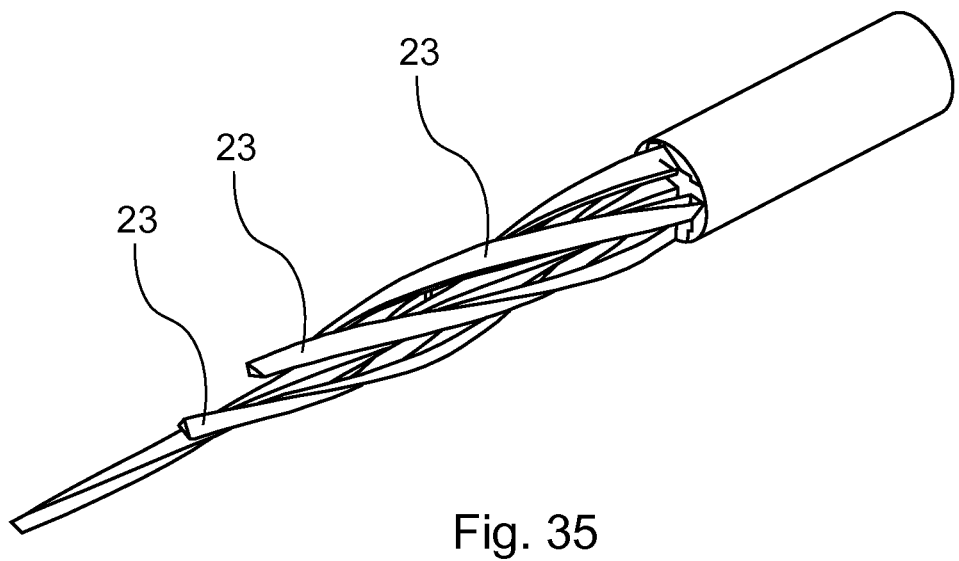
FIG. 35 is a view of an alternative embodiment of the instrument illustrated by FIG. 27.

As already mentioned, the elastic arms 23 (or external arms) can have lengths different from those of the "driver" arm 230 and also between one another (FIG. 35).

Figure 9:
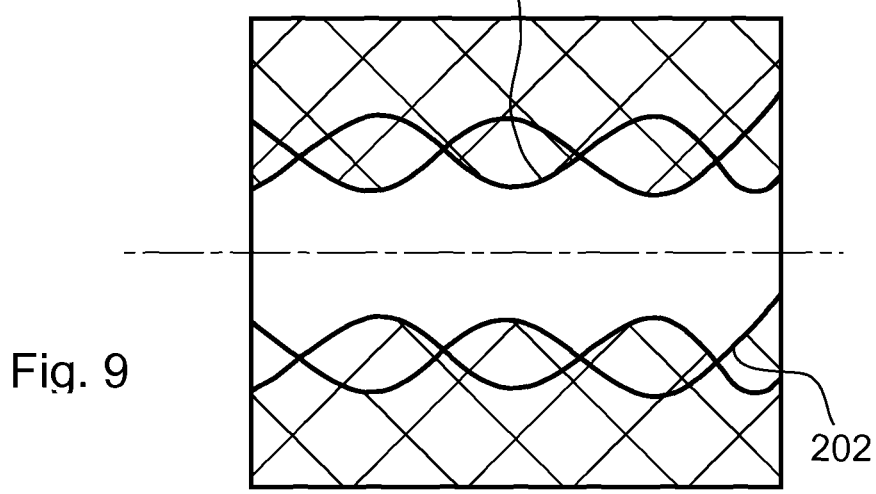
FIG. 9 is a schematic illustration of the internal shape of an endodontic instrument obtained from a blank such as that illustrated by FIG. 5, seen during the rotation of the instruments.
Figure 10:
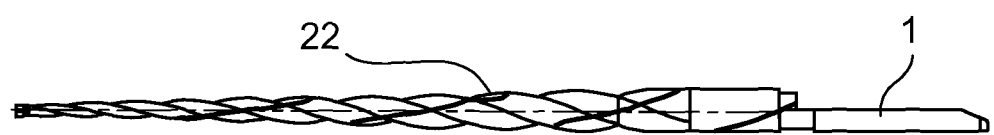
FIGS. 10 to 13 are views of an endodontic instrument in a third embodiment of the disclosure, respectively seen from the side, in a longitudinal view, in a detailed view and in perspective.

By way of an indication, FIG. 9 shows the interior shapes resulting from setting the instrument in rotation (without axial movement), the shape 201 being the shape for one sense of rotation of the tool and the shape 202 being the shape for the reverse sense of rotation.

In the two embodiments that have just been described, the slots 21 have:
- a radial opening (slots 21 communicating with the central hollow feature of an instrument in the case of the instrument illustrated by FIGS. 1 to 4 and the slots being diametrical in the case of the example illustrated by FIGS. 5 to 8);
- an axial opening, the slots 21 extending until they open out at the distal end 20 of the instrument.

It can however be envisaged that the slot or slots will made in a solid rod in extending along a depth smaller than the diameter of the cutting portion. It can furthermore be envisaged that the slot or slots 21 will extend only on one part of the length of the cutting portion, the slot or slots then having no axial opening.

In general, the principle of the disclosure can be applied to all shapes of blanks, including conical, pyramid, cylindrical, polygonal and helical shapes.

Furthermore, the slots made can have shapes different from those that have just been mentioned (helical and sinusoidal), such as:
- rectilinear;
- oblique;
- curved;
- non-straight, especially the shape of an L, S, T, U, V, W, Y or Z.

Furthermore, the slots can have numerous combinations and/or variants, among them:
- the number of slots can vary conventionally from 1 to 6 for a given section, or even more than six, especially for a large-diameter instrument;
- the slot or slots made can have a constant, variable or progressive width;
- the slots may be identical or different;
- the slots can be through-slots or not through-slots (diametrically with a solid rod or even radially with a hollow rod) on all or part of the length of the cutting portion;
- the slots, when they are not through-slots (similar to grooves) can have a depth and/or a width that is constant or variable;
- the slots can be bordered by surfaces provided with relief features such as streaks, pins, notches, bumps, of all dimensions and layouts that can be envisaged;
- the slots can be bordered by surfaces that have undergone specific treatment such as the addition of materials, chemical treatment, coloring;
- at least one given slot can possibly be entirely or partly discontinuous (with at least one solid part on a length, a width and a thickness that is greater or smaller than the slot, the solid part being of any shape, regular or irregular). This type of embodiment can make it possible for example to regulate in a controlled way and therefore to facilitate, reduce, block or guide a flow of fluid at all points of the slot.

Besides, the disclosure can be applied to instruments having shape or dimensional characteristics that are varied, having characteristics belonging especially to the following group:
- the instrument is made out of a blank in the shape of a solid rod or a tube which may be rectilinear or twisted (or have any unspecified shape);
- in a case of an externally machined blank, the number of flutes on a given section classically ranges from one to six (but may exceed six, especially for a large-diameter instrument);
- the endodontic instrument may have classic conicity of 0 to 15% capable of going up to 30% or even more;
- the diameter of the instrument classically ranges from 0.06 mm to 1.2 mm but may go up to 4 mm in the case of veterinary use for example, or may even be smaller than 0.06 mm at the tip;
- the instrument has a length conventionally ranging from 15 to 30 mm, but may more generally vary from 5 mm to 200 mm;
- the instrument is intended for manual or mechanized use and may have a means for fitting on;
- the instrument can be intended for continuous rotary use, or alternate rotary use or in vibratory mode or even for a combination of these uses;
- the instrument can be metallic (made of nickel-titanium or other possible alloys, stainless steel, carbide, or any other metals as the case may be), or even made of plastic.

The designing of the instrument can be adapted to the purpose of the instrument: as an instrument for drilling, catheterization, irrigation or again as a compactor, extractor, trepan, etc.

Referring to FIGS. 10 to 17, a description is provided here below of another endodontic instrument according to the disclosure.

According to the principle of the disclosure, the instrument has a base 1 from which there extends an active part consisting of a cutting portion formed by flutes 22 each demarcated by two cutting edges 220. The flutes 22 are herein helical in shape.

Figure 11:
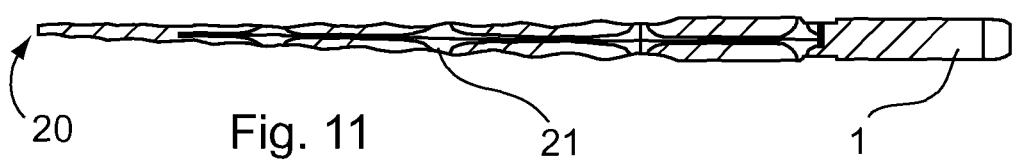

As can be seen in FIG. 11, the slot 21 extends on one part only of the length of the cutting portion and therefore does not open out at the level of the distal end 20 of the instrument.

Figure 15:
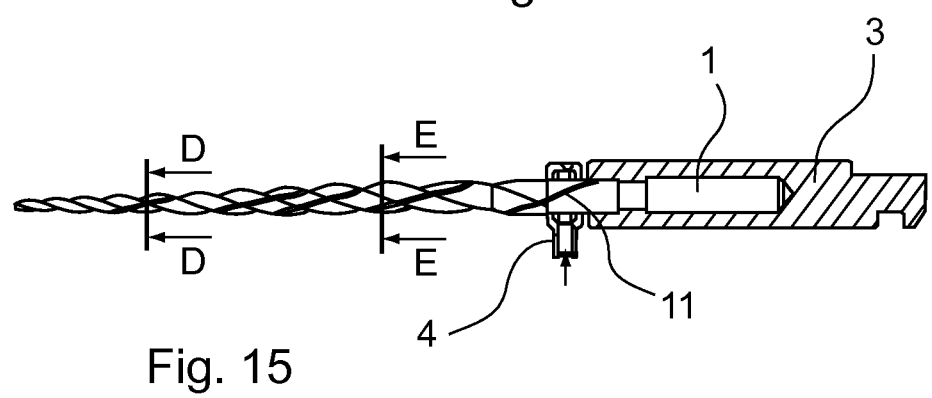
FIG. 15 is a view of the endodontic instrument illustrated by FIG. 10 associated with another type of mechanized sleeve.
Figure 16:
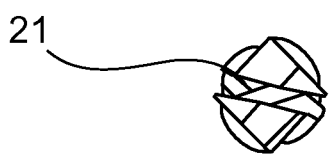
FIGS. 16 and 17 are each a view in cross-section of the endodontic instrument illustrated by FIG. 15.
Figure 17:
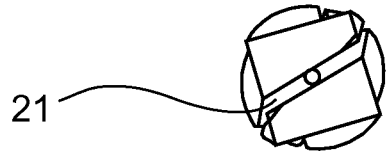

According to the present embodiment, the slot 21 extends along a helical path, passing through the section of the tool, as can be seen in FIG. 16 (which is a view along the section DD indicated in FIG. 15) and FIG. 17 (which is a view along the section EE in FIG. 15).

Figure 12:
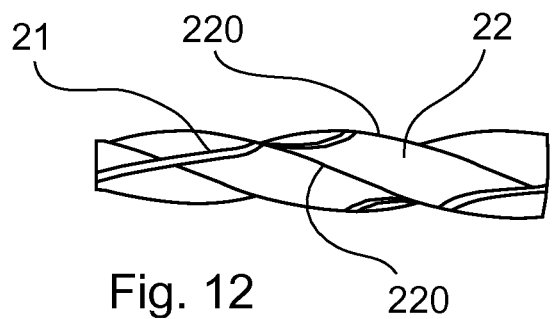
Figure 13:
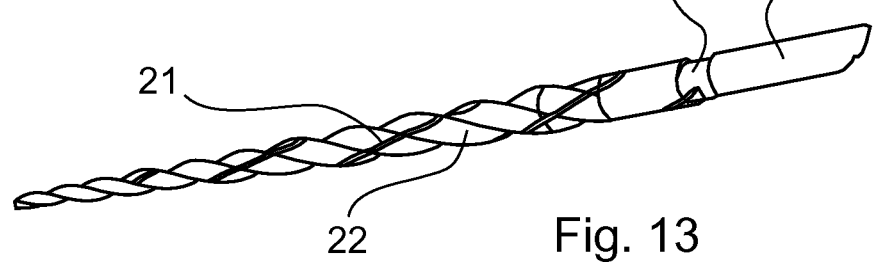

Furthermore, as can be seen more clearly in the detailed view provided by FIG. 12, the helix of the flutes 22 and the helix of the slot 21 have inverse orientations (left and right). By way of an indication, the helix of the flutes is herein oriented to the right while the helix of the slot is mounted to the left.

This designing of the helical shapes of the flutes and the slot in opposite senses enables an efficient combination of the inlet of an irrigation fluid through the interior of the instrument and the removal of dental debris through the exterior of the instrument.

Figure 14:
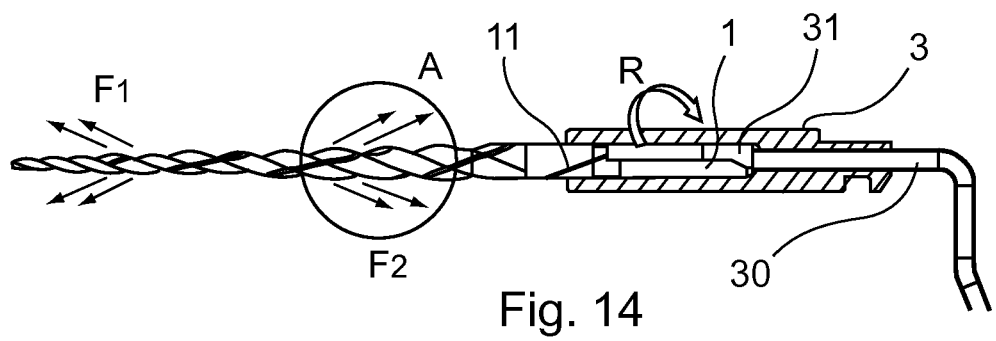
FIG. 14 is a view of the endodontic instrument illustrated by FIG. 10, associated with a mechanized sleeve.

This is illustrated by FIG. 14 which shows an endodontic instrument in which the flutes extend in a helical shape with a right-hand pitch while the slot 21 extends in a helical shape with a left-hand pitch. When this instrument is driven rotationally in the clockwise sense as indicated by the arrow R, the active part of the instrument tends to push the fluid towards the bottom of the canal as indicated by the arrows F1 and removes the dentinal debris through the exterior of the instrument as indicated by the arrows F2.

Figure 18:
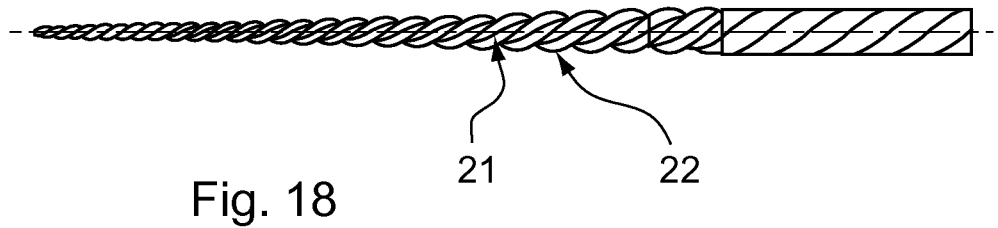
FIG. 18 is a side view of an endodontic instrument according to a fourth embodiment of the disclosure.
Figure 19:
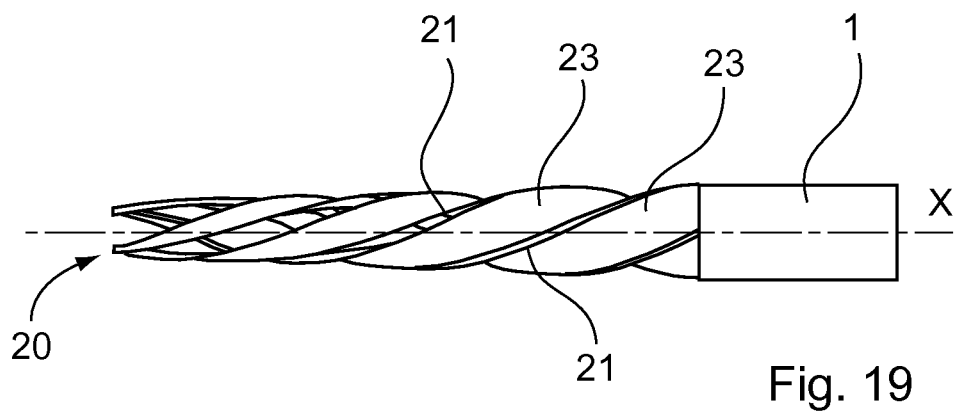
FIGS. 19 and 20 are views of an endodontic instrument according to a fifth embodiment of the disclosure seen respectively in a side view and in perspective.

According to one variant that can be envisaged, illustrated in FIG. 18, the cutting portion can be made in such a way that the helix of the slot 21 and the helix of the flutes 22 are made in the same sense (the right-hand pitch in both cases and the left-hand pitch in both cases). Such a configuration gives rise to greater thrust of fluid because the two dynamics, namely the internal and external dynamics, are combined in a synergic manner.

According to yet another variant, the helix of the longitudinal slot can have alternately one right-hand pitch and one left-hand pitch along the instrument, thus driving respective simultaneous motions of radial contraction and expansion of the instrument rotating inside the channel. Such a design makes it possible to influence the dynamics of the fluid according to specific parameters of the instrument, the fluid and the rotation of the instrument, leading to the generation of a movement of the fluid in one sense and with a controlled flow rate which may or may not be constant, and may or may not be continuous. Such a geometry can also be used with instruments whose mobility is other than continuously rotational, such as manual instruments, alternating rotary instruments, vibrating instruments, etc.

With respect to the flutes, it can be noted that they can be partially or totally helical, continuous or alternating. In general, if the sense of rotation of the instrument is clockwise, flutes are made in such a way that the sense of the helix of the flutes is rightward for the drilling instruments and leftward for the compacting instruments. The pitch of the helix of the slots may for its part be constant, variable or progressive.

Besides, the flutes and/or the cutting edges can be provided with relief features.

According to another advantageous characteristic, the instrument can be made in such a way that its base 1 has at least one slot 11 communicating with the slot or slots 21 of the active part of the instrument which is constituted as it happens by the cutting portion 2.

Thus, the slot or slots made on the base 1 of the tool can be used to connect the irrigation system of the instrument constituted by the slot or slots 21 with an external device.

As illustrated by FIG. 14, such an external device can be a mechanized sleeve coupled to a conduit 30 for conveying a fluid, this conduit 30 extending, according to the present embodiment, axially in relation to the axis of the mechanized sleeve and communicating with a chamber 31 of the mechanized sleeve, itself in communication with the slot 11 of the base of the instrument.

According to the embodiment shown in FIG. 15, the base of the instrument is coupled with a mechanized sleeve 3 and a fluid-conveying device 4 is attached to the part of the base 1 extending outside the sleeve 3. This device 4 is planned so as to radially convey the irrigation fluid in the slot 11 of the base 1 of the instrument.

According to one particular embodiment illustrated by FIGS. 19 to 26, two slots 21 are made and the active part of the instrument has four arms 23. According to another particular embodiment, not shown, two slots 21 are made and the active part of the instrument has three arms 23.

The disposition of the slots relative to one another influences on the quantity of arms generated.

As can be seen, the slots 21 extend from the base 1 in presenting an increasing width in going towards the distal end of the instrument. This is illustrated by FIG. 22 (which is a view along the section AA indicated in FIG. 21) and FIG. 23 (which is a view along the section BB indicated in FIG. 21) which shows a slot with a width 21 particularly greater in FIG. 22 than the width of the slot 21 shown in FIG. 23 (FIG. 24 being a view along the section CC indicated in FIG. 21, i.e. at the base 1 of the instrument).

The slots 21 of the instrument extend longitudinally along a helical path.

The arms 23 take the form of ribbons extending helically around the axis of rotation X of the instrument and are thus borne by a load-bearing core extending along a helical path (the load-bearing core being the line connecting the central points of all the cross-sections of an arm). The number of arms can vary. They may be of a constant, variable or progressive width, of greater or smaller thickness, greater smaller width, greater or smaller length, depending on need in order to adapt the instrument to the morphology of the dental canals, especially conical canals.

Such an instrument with its arms carried by a load-bearing core extending helically, is capable of undergoing volumetrical variations.

Figure 20:
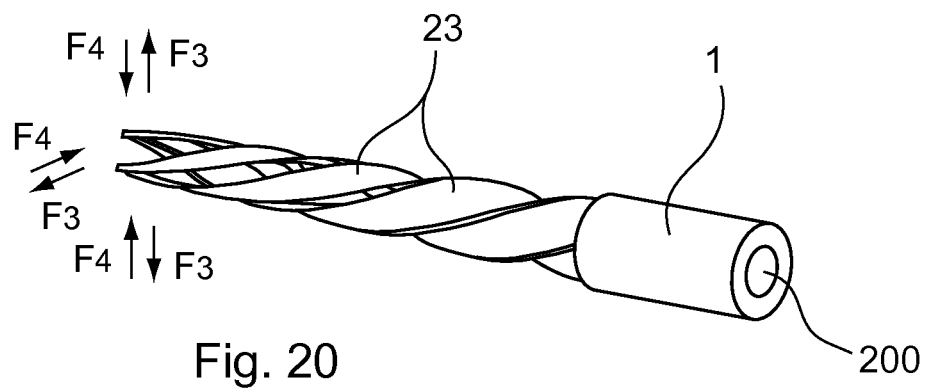
Figure 21:
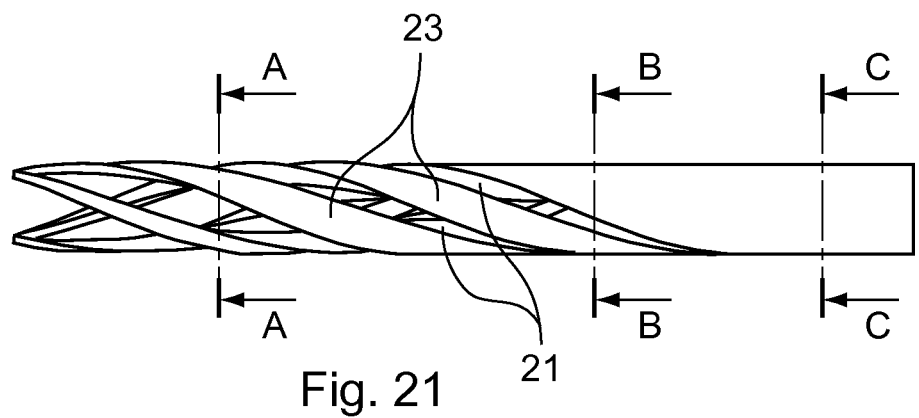

Indeed, in the case of an instrument having an arm for which the load-bearing core extends along a helical path with a left-hand pitch as illustrated in FIG. 20, a rotation in the clockwise sense of the instrument will tend to give rise to an expansion of the arms when there is a resistant torque as illustrated by the arrows F3 while a rotation in the counter-clockwise of the instrument will tend to give rise to a retraction of the arms when there is a resistant torque as illustrated by the arrows F4 tending to lead the active part of the instrument into a configuration as illustrated by FIG. 25 in which the arms are attached to one another.

Furthermore, the helical arms 23 can be of greater or lesser length and especially of different lengths as illustrated in FIG. 26, in order to match the shape of the active part to the conical shape of the canal.

As shown in FIG. 20, the arms 23 demarcate an axial hollow feature which extends and communicates with the axial hollow feature 200 made in the base 1, in order to enable and facilitate the flow of an irrigation fluid inside the instrument.

Besides, these free ends of the arms can be identical to or different from one another. They can for example be pointed in shape, flat, rounded, skewed, conical, pyramid shaped, etc.

Figure 33:
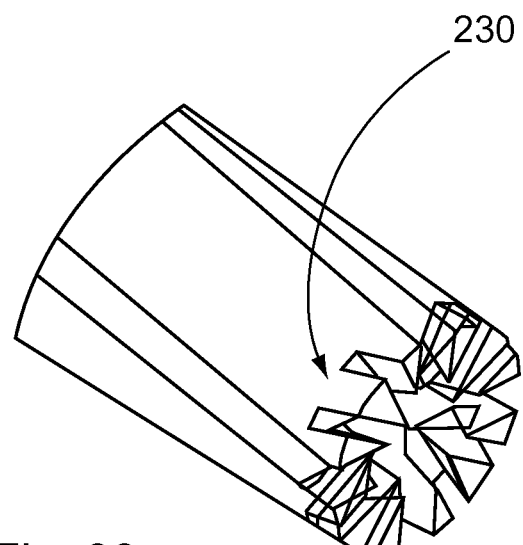
FIG. 33 is a view of another variant of the endodontic instrument, FIG. 34 being a view of the instrument illustrated by FIG. 33, according to one example of use.

Besides, they may take the form of a notched end 230 as illustrated in FIG. 33, the arms thus ending in the form of claws. The teeth forming the toothed end 230 can have a triangular section, one of whose tips is directed towards the axial hollow feature of the instrument.

Figure 34:
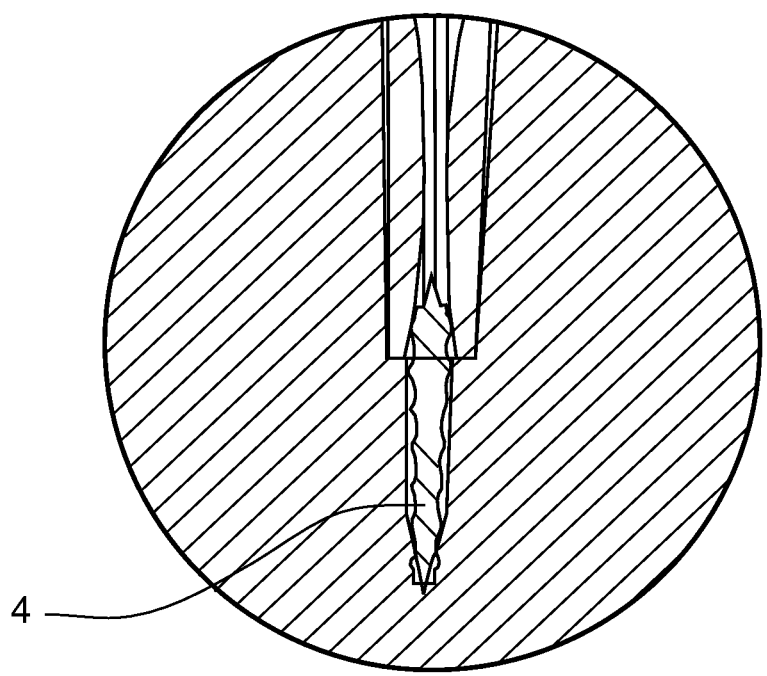

Thus, such an instrument can be used to grip an undesirable element 5 (FIG. 34) such as an instrument broken in a dental tooth canal.

Indeed, as indicated here above, the rotation of the instrument can enable a radial expansion in one sense and a radial retraction in the other sense. The instrument can thus be introduced into the root canal in the sense of a radial expansion until the fragment to be extracted is reached, and then instrument can be withdrawn rotationally in the opposite direction, to enable its retraction on the fragment 4 and therefore to enable it to be gripped and clamped.

Similarly, it can also be envisaged to use an instrument of this kind to carry out a removal of tissue (a biopsy).

Although the present disclosure has been described with reference to exemplary and preferred embodiments, workers skilled in the art will recognize that changes may be made in form and detail without departing from the spirit and scope of the disclosure.

The invention claimed is:

1. Endodontic instrument for working a canal in a tooth, comprising:
    a base forming a non-cutting portion and comprising an irrigation slot configured to receive an irrigation fluid;
    a distal end; and
    an active part forming a cutting portion longitudinally extending from the base to the distal end for working of the canal, wherein said active part has a plurality of slots formed on an exterior surface of the active part and passing through a cross-section of the active part, the plurality of slots extending longitudinally and forming passages for the irrigation fluid, the irrigation slot in the base communicating with at least one of the plurality of slots in the active part, wherein said active part has at least two demarcating arms extending longitudinally from the base to the distal end in the form of ribbons, wherein each of the plurality of slots is delimited between two adjacent arms of said at least two demarcating arms at least at the exterior surface, the plurality of slots extending continuously along an entire length of the active part.

2. Endodontic instrument according to claim 1, wherein at least one of said at least two demarcating arms comprises at least one flute between two cutting edges, said flute extending longitudinally along the cutting portion.

3. Endodontic instrument according to claim 1, wherein each of said plurality of slots is helical.

4. Endodontic instrument according to claim 1, wherein each of the plurality of slots has a shape belonging to the following group consisting of: sinusoidal, rectilinear, oblique, curved, and non-straight.

5. Endodontic instrument according to claim 1, wherein each of said plurality of slots has a radial opening.

6. Endodontic instrument according to claim 1, wherein each of said plurality of slots has an axial opening at the distal end.

7. Endodontic instrument according to claim 1, wherein the base has an axis of rotation, and each of said plurality of slots extends longitudinally so as to be centered about said axis of rotation.

8. Endodontic instrument according to claim 1, wherein the base has an axis of rotation, and each of said plurality of slots extends longitudinally so as to be off-centered relative to said axis of rotation.

9. Endodontic instrument according to claim 1, wherein the irrigation slot radially conveys the irrigation fluid relative to an axis of the instrument.

10. Endodontic instrument according to claim 1, wherein each of said at least two demarcating arms is borne by a load-bearing core extending along a path that is at least partially helical.

11. Endodontic instrument according to claim 1, wherein said at least two demarcating arms demarcate an axial hollow feature.

12. Endodontic instrument according to claim 11, wherein said axial hollow feature demarcated by said at least two demarcating arms communicates with an axial hollow feature defined in said base.

13. Endodontic instrument according to claim 1, wherein said at least two demarcating arms have different lengths.

14. Endodontic instrument according to claim 13, wherein one of said at least two demarcating arms is a central arm with a length greater than that of the rest of said at least two demarcating arms.

15. Endodontic instrument according to claim 1, wherein each of said at least two demarcating arms has a notched end.

16. Endodontic instrument of claim 1, wherein said at least two demarcating arms are cantilevered from the base and disconnected from one another at their distal ends.

17. Endodontic instrument of claim 1, wherein the at least two demarcating arms are configured to enable a volumetric variation in the active part.

18. An endodontic instrument for working a canal in a tooth, comprising:
    a base constituting a grasping end configured to be manipulated by hand by a practitioner or to be mounted to a rotating tool, the base comprising a non-cutting portion and an irrigation slot configured to receive an irrigation fluid;
    a distal end; and
    an active part forming a cutting portion longitudinally extending from the base to the distal end for working of the canal, wherein said active part has a plurality of slots formed on an exterior surface of the active part and passing through a cross-section of the active part, the plurality of slots extending longitudinally and forming passages for the irrigation fluid, the irrigation slot in the base communicating with at least one of the plurality of slots in the active part, wherein said active part has at least two demarcating arms extending longitudinally from the base to the distal end in the form of ribbons, wherein each of the plurality of slots is delimited between two adjacent arms of said at least two demarcating arms at least at the exterior surface, the plurality of slots extending continuously along an entire length of the active part.

19. Endodontic instrument according to claim 1, wherein said base constitutes a grasping end configured to be manipulated by hand by a practitioner or to be mounted to a rotating tool.

\* \* \* \* \*